United States Patent [19]
Gallagher et al.

[11] Patent Number: 6,075,039
[45] Date of Patent: Jun. 13, 2000

[54] 5HT RECEPTOR BINDING BENZIMIDAZOLYLPIPERIDINES

[75] Inventors: Peter Thaddeus Gallagher, Yateley; Martin Victor Miles, Twickenham; William Martin Owton, Lightwater; Colin William Smith, Bracknell, all of United Kingdom

[73] Assignee: Eli Lilly and Company Limited, Basingstoke, United Kingdom

[21] Appl. No.: 08/880,450

[22] Filed: Jun. 24, 1997

[30] Foreign Application Priority Data

Jun. 26, 1996 [GB] United Kingdom ................... 9613423

[51] Int. Cl.[7] ....................... A61K 31/445; C07D 401/06
[52] U.S. Cl. ............................................. 514/322; 546/199
[58] Field of Search ............................... 514/322; 548/199

[56] References Cited

U.S. PATENT DOCUMENTS

| | | | |
|---|---|---|---|
| 4,035,369 | 7/1977 | Vandenberk et al. | 514/322 |
| 4,254,127 | 3/1981 | Vandenberk et al. | 514/322 |
| 4,680,296 | 7/1987 | Manoury et al. | 514/259 |
| 5,114,949 | 5/1992 | Gueremy et al. | 514/293 |
| 5,652,246 | 7/1997 | de Nanteuil et al. | 514/300 |
| 5,661,169 | 8/1997 | DiMalta et al. | 514/387 |

FOREIGN PATENT DOCUMENTS

| | | | |
|---|---|---|---|
| WO 95/03298 | 2/1995 | European Pat. Off. | 401/6 |
| WO 96/04287 | 2/1996 | European Pat. Off. | |
| 1 532 546 | 11/1978 | United Kingdom | 401/69 |

OTHER PUBLICATIONS

Fukuda et al. "Preparation of perhydrobenzimidazolone derivatives as antipsychotics" CA 127:3311488, 1997.

Peroutka et al. "Serotonin receptor families in the central nervous system an overview" Ann. N. Y. Aca. Sci. v. 600, 104–107, 1990.

Patent Abstracts of Japan, vol. 11, No. 69, JP 61 227565, 1986.

Malleron, et al., *J. of Med. Chem.*, vol. 36, pp. 1194–1202, 1193.

*Primary Examiner*—Ceila Chang
*Attorney, Agent, or Firm*—Alexander Wilson; Paul J. Gaylo

[57] ABSTRACT

A pharmaceutical compound of the formula

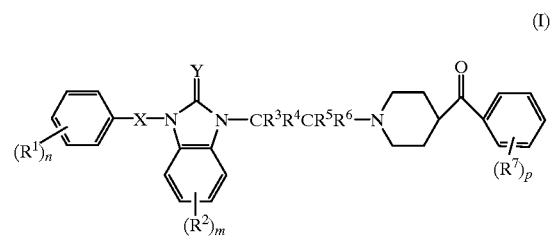

in which X is —CR'R"— or —C(O)— where R' and R" are each hydrogen, $C_{1-6}$ alkyl or optionally substituted phenyl, Y is oxygen or sulphur, $R^1$, $R^2$ and $R^7$ are each selected from halo, $C_{1-4}$ alkyl, $C_{1-4}$ alkoxy, trifluoromethyl, nitro, cyano, amino, phenyl, phenoxy, benzyl, benzyloxy, acylamino, $C_{1-4}$ alkylsulphonylamino, $C_{1-4}$ alkylthio, $C_{1-4}$ alkylsulphonyl, carboxamido, sulphonamido, hydroxy, methylenedioxy, carboxy, and heteroaryl, $R^3$, $R^4$, $R^5$ and $R^6$ are each hydrogen, $C_{1-6}$ alkyl or optionally substituted phenyl, n, m and p are each 0, 1, 2 or 3;

or a salt or ester thereof.

6 Claims, No Drawings

5HT RECEPTOR BINDING BENZIMIDAZOLYLPIPERIDINES

This invention relates to pharmaceutical compounds, their preparation and use. Certain 1-benzazolylalkyl-4-substituted-piperidines are disclosed in British Patent 1 532 546.

The compounds of the invention are of the formula:

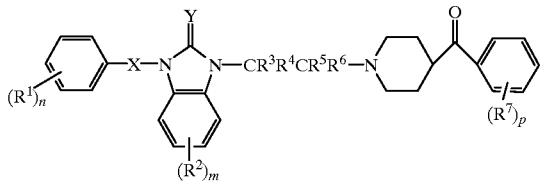

(I)

in which X is —CR'R"— or —C(O)— where R' and R" are each hydrogen, $C_{1-6}$ alkyl or optionally substituted phenyl, Y is oxygen or sulphur, $R^1$, $R^2$ and $R^7$ are each selected from halo, $C_{1-4}$ alkyl, $C_{1-4}$ alkoxy, trifluoromethyl, nitro, cyano, amino, phenyl, phenoxy, benzyl, benzyloxy, acylamino, $C_{1-4}$ alkylsulphonylamino, $C_{1-4}$ alkylthio, $C_{1-4}$ alkylsulphonyl, carboxamido, sulphonamido, hydroxy, methylenedioxy, carboxy, and heteroaryl, $R^3$, $R^4$, $R^5$ and $R^6$ are each hydrogen, $C_{1-6}$ alkyl or optionally substituted phenyl, n, m and p are each 0, 1, 2 or 3;
and salts and esters thereof.

The group X is —CR'R"— or —C(O)—, and is preferably —CH$_2$—, and the value of Y is preferably oxygen.

Preferred values of $R^1$ are halo especially fluoro, heterocyclyl, $C_{1-4}$ alkyl, $C_{1-4}$ alkoxy, cyano, nitro, carboxy, amino, carboxamido and acetamido, and n is 0, 1 or 2. The benzimidazolone nucleus can be substituted and $R^2$ is preferably halo, $C_{1-4}$ alkoxy, hydroxy, and m 0, 1 or 2. The group $R^7$ is preferably halo especially fluoro, difluoro or chloro, and p 0, 1 or 2.

It is most preferred that n and p are 1 and m is 0, and it will be appreciated that when n, m or p is 2 or 3 the values of $R^1$, $R^2$ and $R^7$, on each ring, can be different.

A particular group of compounds is one in which $R^1$, $R^2$ and $R^7$ are each selected from halo, $C_{1-4}$ alkyl, $C_{1-4}$ alkoxy, trifluoromethyl, nitro, cyano, amino, phenyl, phenoxy, benzyl, benzyloxy, acylamino, $C_{1-4}$ alkylsulphonylamino, $C_{1-4}$ alkylthio, $C_{1-4}$ alkylsulphonyl, carboxamido, hydroxy, methylenedioxy, carboxy, and heteroaryl.

The compounds of the invention are indicated for use in the treatment of disorders of the central nervous system. They are active in tests that indicate serotonergic modulation.

In the above formula (I), a $C_{1-4}$ alkyl group includes methyl, ethyl, propyl, isopropyl, butyl and tert. butyl, and is preferably methyl or ethyl. A $C_{1-4}$ alkoxy group is one such alkyl group linked to a ring via an oxygen atom, and a halo atom is preferably chlorine, bromine or fluorine, and especially chlorine or fluorine. A substituted phenyl group is phenyl substituted with one or more, for example one to three, substituents selected from, for example $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy and $C_{1-4}$ alkoxycarbonyl. A heteroaryl group includes the oxadiazole substituent, in particular 1,2,4-oxadiazol-3-yl and 1,3,4-oxadiazol-3-yl, optionally substituted by $C_{1-4}$ alkyl as, for example, 5-methyl-1,2,4-oxadiazol-3-yl and 5-methyl-1,3,4-oxadiazol-3-yl. Also included in the term heteroaryl are the following groups: 2-thienyl, 3-thienyl, 2-pyridyl, 3-pyridyl, 4-pyridyl, 2-benzothienyl, 3-benzothienyl, 2-quinolinyl, 3-quinolinyl, 4-quinolinyl, 2-benzofuranyl, 3-benzofuranyl, 2-benzimidazolyl, 2-furanyl or 3-furanyl. A naphthyl group is attached at the 1- or 2-position. Such groups are preferably unsubstituted.

A preferred group of compounds of the invention is of the formula:

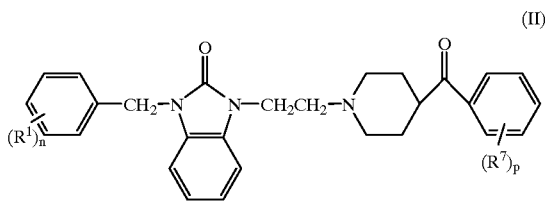

(II)

in which $R^1$ is halo, heterocyclyl, $C_{1-4}$ alkyl, $C_{1-4}$ alkoxy, cyano, nitro, carboxy, carboxamido or acetamido, $R^7$ is halo, and n and p are 1; and salts and esters thereof.

It will be appreciated that the compounds of the invention can contain one or more asymmetric carbon atoms which give rise to isomers. The compounds are normally prepared as racemic mixtures and can conveniently be used as such, but individual isomers can be isolated by conventional techniques if so desired. Such racemic mixtures and individual optical isomers form part of the present invention. It is preferred to use an enantiomerically pure form.

It is, of course, possible to prepare salts of the compounds of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, phosphoric acid, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

The compounds can be utilised in ester form, such esters being aliphatic or aromatic, such as, for example, alkyl and phenolic esters. The most preferred esters are alkyl esters derived from $C_{1-4}$ alkanols, especially methyl and ethyl esters.

The invention also includes a process for producing a compound of formula (I) above, which comprises reacting a compound of the formula:

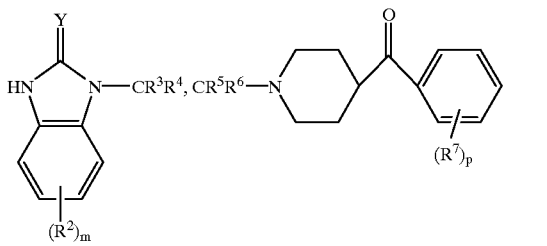

with a compound of formula:

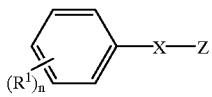

where the substituents and n, m and p have the values given above for formula (I), and Z is a leaving group.

The reaction is preferably carried out in an inert organic solvent such as, for example, DMF or N-methylpyrrolidinone, and at a temperature of from 0° C. to 100° C. The reaction takes place in alkaline conditions by the use of, for example, a strong base such as sodium hydride. Alternatively, compounds of the reaction can be made by condensing a compound of the formula:

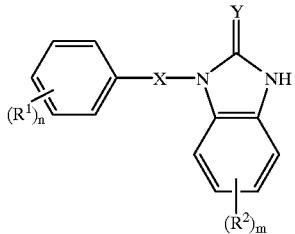

with a compound of the formula:

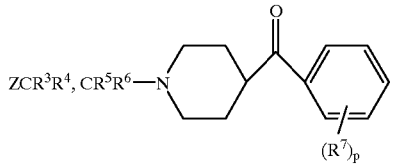

under similar reaction conditions.

Compounds of formula (III) are either known or can be preferred by methods well known in the art as, for example, described in U.S. Pat. No. 4,035,369.

As mentioned above, the compounds of the invention have useful central nervous system activity. The compounds are active at the serotonin, $5\text{-HT}_{1D}$, receptor. Their binding activity has been demonstrated in a test described by Zgombick, J. M. et al., Molecular Pharmacology Vol. 40 1992, pages 1036–1042, and compounds of the invention as described in the following Examples have a Ki of from 1 nM to 200 nM. Some of the compounds, for example those of formula III, also possess binding activity at the $5\text{-HT}_{1B}$ receptor. Furthermore, compounds have activity at the 5-HT2A receptors as shown in the test described by Leysen, J. E. et al., Molecular Pharmacology Vol. 21 1981, pages 301–314.

Because of their selective affinity for the 5-HT receptors, the compounds of the present invention are indicated for use in treating a variety of conditions such as obesity, bulimia, alcoholism, pain, depression, hypertension, ageing, memory loss, sexual dysfunction, anxiety, schizophrenia, gastrointestinal disorders, headache, cardiovascular disorders, smoking cessation, drug addiction, emesis, Alzheimer's disease and sleeping disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or solvate thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Examples illustrate the invention:

EXAMPLE 1

1-[2-[4-(4-Fluorobenzoyl)-1-piperidinyl]-1-ethyl]-3-phenylmethyl-1,3-dihydro-2H-benzimidazol-2-one hydrochloride.

1-[2-[4-(4-Fluorobenzoyl)-1-piperidin-yl]-1-ethyl)-1,3-dihydro-2H-benzimidazol-2-one (German Patent 2,645,125 (CA 87 102,326)) (1 g, 2.747 mmol) in DMF (10 ml) was added to an unwashed suspension of sodium hydride (50%, 0.144 g, 3 mmol) in DMF (10 ml) and stirred for 2 hours at room temperature under nitrogen. To this mixture was added benzyl bromide (0.356 ml, 0.5122 g, 3 mmol) and the resultant mixture stirred at room temperature for 24 hours. The DMF was evaporated in vacuo at 50° C. and the residue dissolved in ethyl acetate (30 ml). The ethyl acetate solution was treated with 0.5M hydrochloric acid and a white precipitate was thrown down from the bi-phasic mixture. This precipitate was isolated by filtration, washed with diethyl ether to give 1-[2-[4-(4-fluorobenzoyl)-1-piperidinyl]-1-ethyl]-3-phenylmethyl-1,3-dihydro-2H-benzimidazol-2-one hydrochloride, m.p. 195–197° C.

The following compounds were similarly prepared:

1-[2-[4-(4-Fluorobenzoyl)-1-piperidinyl]-1-ethyl]-3-(4-trifluoromethylphenyl)methyl-1,3-dihydro-2H-benzimidazol-2-one hydrochloride, m.p. 195–199° C.

1-[2-[4-(4-Fluorobenzoyl)-1-piperidinyl]-1-ethyl]-3-(4-methylphenyl)methyl-1,3-dihydro-2H-benzimidazol-2-one hydrochloride, m.p. 184–186° C.

1-[2-[4-(4-Fluorobenzoyl)-1-piperidinyl]-1-ethyl]-3-(4-methoxyphenyl)methyl-1,3-dihydro-2H-benzimidazol-2-one hydrochloride, m.p. 198–200° C.

1-[2-[4-(4-Fluorobenzoyl)-1-piperidinyl]-1-ethyl]-3-(4-fluorophenyl)methyl-1,3-dihydro-2H-benzimidazol-2-one hydrochloride, m.p. 212° C.

1-[4-(1,1-Dimethylethylphenyl)methyl]-3-[2-[4-(4-fluorobenzoyl)-1-piperidinyl]-1-ethyl]-1,3-dihydro-2H-benzimidazol-2-one hydrochloride, m.p. 228° C.

1-(3,4-Dichlorophenyl)methyl-3-[2-[4-(4-fluorobenzoyl)-1-piperidinyl]-1-ethyl]-1,3-dihydro-2H-benzimidazol-2-one hydrochloride, m.p. 204–206° C.

1-[2-[4-(4-Fluorobenzoyl)-1-piperidinyl]-1-ethyl]-3-(4-iodophenyl)methyl-1,3-dihydro-2H-benzimidazol-2-one hydrochloride, m.p. 182–184° C.

1-(4-Chlorophenyl)methyl-3-[2-[4-(4-fluorobenzoyl)-1-piperidinyl]-1-ethyl]-1,3-dihydro-2H-benzimidazol-2-one hydrochloride, m.p. 178–180° C.

1-(3-Chlorophenyl)methyl-3-[2-[4-(4-fluorobenzoyl)-1-piperidinyl]-1-ethyl]-1,3-dihydro-2H-benzimidazol-2-one hydrochloride, m.p. 185–190° C.

1-(2-Chlorophenyl)methyl-3-[2-[4-(4-fluorobenzoyl)-1-piperidinyl]-1-ethyl]-1,3-dihydro-2H-benzimidazol-2-one hydrochloride, m.p. 206–210° C.

1-[2-[4-(4-Fluorobenzoyl)-1-piperidinyl]-1-ethyl]-3-(4-phenylmethoxyphenyl)methyl-1,3-dihydro-2H-benzimidazol-2-one hydrochloride, m.p. 190–192° C.

1-(4-Cyanophenyl)methyl-3-[2-[4-(4-fluorobenzoyl)-1-piperidinyl]-1-ethyl]-1,3-dihydro-2H-benzimidazol-2-one hydrochloride, m.p. 206–208° C.

1-[2-[4-(4-Fluorobenzoyl)-1-piperidinyl]-1-ethyl]-3-(4-nitrophenyl)methyl-1,3-dihydro-2H-benzimidazol-2-one hydrochloride, m.p. 135–137° C.

1-[2-[4-(4-Fluorobenzoyl)-1-piperidinyl]-1-ethyl]-3-(3-trifluoromethylphenyl)methyl-1,3-dihydro-2H-benzimidazol-2-one hydrochloride, m.p. 184–188° C.

1-[2-[4-(4-Fluorobenzoyl)-1-piperidinyl]-1-ethyl]-3-(2-methoxyphenyl)methyl-1,3-dihydro-2H-benzimidazol-2-one hydrochloride, m.p. 219° C.

1-[2-[4-(4-Fluorobenzoyl)-1-piperidinyl]-1-ethyl]-3-(2-fluorophenyl)methyl-1,3-dihydro-2H-benzimidazol-2-one hydrochloride, m.p. 221° C.

1-[2-[4-(4-Fluorobenzoyl)-1-piperidinyl]-1-ethyl]-3-(3,4-methylenedioxyphenyl)methyl-1,3-dihydro-2H-benzimidazol-2-one hydrochloride, m.p. 204–206° C.

1-[2-[4-(4-Fluorobenzoyl)-1-piperidinyl]-1-ethyl]-3-(3-(methoxyphenyl)methyl-1,3-dihydro-2H-benzimidazol-2-one hydrochloride, m.p. 189–193° C.

Methyl 4-[[3-[2-[4-(4-fluorobenzoyl)-1-piperidinyl]-1-ethyl]-1,3-dihydro-2H-2-oxo-benzimidazol-1-yl]methyl]benzoate hydrochloride, m.p. 198–200° C.

1-(3-Cyanophenyl)methyl-3-[2-[4-(4-fluorobenzoyl)-1-piperidinyl]-1-ethyl]-1,3-dihydro-2H-benzimidazol-2-one hydrochloride, m.p. 209–211° C.

1-[2-[-4-(4-Fluorobenzoyl)-1-piperidinyl]-1-ethyl]-3-(4-methylsulphonylphenyl)methyl-1,3-dihydro-2H-benzimidazol-2-one hydrochloride, m.p. 218–219° C.

1-(4-Acetamidophenyl)methyl-3-[2-[4-(4-fluorobenzoyl)-1-piperidinyl]-1-ethyl]-1,3-dihydro-2H-benzimidazol-2-one, m.p. 90–92° C.

1-[2-[4-(4-Fluorobenzoyl)-1-piperidinyl]-1-ethyl]-3-(3-nitrophenyl)methyl-1,3-dihydro-2H-benzimidazol-2-one hydrochloride, m.p. 166–171° C.

Methyl 3-[[3-[2-[4-(4-fluorobenzoyl)-1-piperidinyl]-1-ethyl]-1,3-dihydro-2H-2-oxo-benzimidazol-1-yl]methyl]benzoate hydrochloride, m.p. 163.5–167° C.

1-[2-[4-(4-Fluorobenzoyl)-1-piperidinyl]-1-ethyl]-3-(2,3-methylenedioxyphenyl)methyl-1,3-dihydro-2H-benzimidazol-2-one hydrochloride, m.p. 198–200° C.

1-[2-[-4-(4-Fluorobenzoyl)-1-piperidinyl]-1-ethyl]-3-(4-methylsulphonylphenyl)methyl-1,3-dihydro-2H-benzimidazol-2-one hydrochloride, m.p. 181–183° C.

EXAMPLE 2

1-Isopropylidenyl-3-[4-(5-methyl-1,2,4-oxadiazol-3-yl)phenyl]methyl-1,3-dihydro-2H-benzimidazol-2-one Sodium (0.102 g, 4.48 mmol) in methanol (15 ml) was added to hydroxylamine hydrochloride(0.312 g, 4.48 mmol) and stirred for one hour at room temperature, filtered, more methanol (15 ml) was added and to the resultant solution was added 1-(4-cyanophenyl)methy-3-isopropylidenyl-1,3-dihydro-2H-benzimidazol-2-one (1.3 g 4.48 mmol) and the mixture heated under reflux during one hour. Another 1 equivalent of hydroxyalmine was prepared (as above) and added to the reaction mixture containing the cyanobenzylbenzimidazol-2-one. This mixture was heated under reflux for 24 hours, the methanol removed in vacuo and the residue azeotroped with toluene (2×40 ml). Acetic anhydride (15 ml) was added and the mixture heated under reflux for a further 24 hours. The acetic anhydride was evaporated in vacuo and water added to the residue followed by chloroform. The organic layer was washed with saturated sodium hydrogen carbonate solution, dried (MgSO$_4$), filtered and evaporated in vacuo to give a dark oil. This oil was chromatographed on silica (10% MeOH, 90% CHCl$_3$) to give the title product.

1-[4-(5-Methyl-1,2,4-oxadiazol-3-yl)phenyl]methyl-1,3-dihydro-2H-benzimidazol-2-one Hydrochloric acid (d=1.84 g/ml, 2 ml) was added to 1-isopropylidenyl-3-[4-(5-methyl-1,2,4-oxadiazol-3-yl)phenyl]methyl-1,3-dihydro-2H-benzimidazol-2-one (0.7 g, 2.02 mmol) in ethanol (10 ml) and allowed to stand at room temperature overnight, the resulting crystals were isolated by filtration, washed with ethanol (3 ml) then ether (20 ml) and dried to yield a pale yellow solid.

1-(2-Chloroethyl)-3-[4-(5-methyl-1,2,4-oxadiazol-3-yl)phenyl]methyl-1,3-dihydro-2H-benzimidazol-2-one 1-[4-(5-Methyl-1,2,4-oxadiazol-3-yl)phenyl]methyl-1,3-dihydro-2H-benzimidazol-2-one (0.416 g, 1.36 mmol) was added to a suspension of 60% sodium hydride (0.06 g, 1.49 mmol, dispersion in oil) in N-methylpyrrolidinone (3 ml) and stirred for 2 hours. More N-methylpyrrolidinone (2 ml) was added followed by 1-bromo-2-chloroethane (0.203 ml, 0.351 g, 2.44 mmol). The resultant mixture was allowed to stir at room temperature for 16 h then water was added and the mixture extracted with ethyl acetate (2×30 ml). The organic layer was washed with water (4×50 ml), brine (50 ml), dried (MgSO$_4$).filtered and evaporated in vacuo to give a light brown oil.

1-[2-[4-(4-Fluorobenzoyl)-1-piperidinyl]-1-ethyl]-3-[4-(5-methyl-1,2,4-oxadiazol-3-yl)phenyl]methyl-1,3-dihydro-2H-benzimidazol-2-one hydrochloride 1-(2-Chloroethyl)-3-[4-(5-methyl-1,2,4-oxadiazol-3-yl)phenyl]methyl-1,3-dihydro-2H-benzimidazol-2-one (0.363 g, 0.983 mmol) 4-fluorobenzoylpiperidine p-toluenesulfonate (0.522 g, 1.38 mmol) potassium carbonate (0.476 g, 3.44 mmol) sodium iodide (0.147 g, 0.983 mmol) and N-methylpyrrolidinone (8 ml) were heated at 80° C. under nitrogen with magnetic stirring overnight. Water was added to the mixture which was then extracted with ethyl acetate (2×50 ml). The combined organic extracts were washed with water (4×50 ml) and brine (50 ml), dried (MgSO$_4$), filtered and evaporated in vacuo to give a brown oil (0.6 g). This oil was chromatographed on silica with chloroform/methanol and the resultant solid converted to a hydrochloride which was washed with ethyl acetate/ether to yield a white crystalline solid, m.p. 214–216° C.

EXAMPLE 3

1-(4-Cyanophenyl)methyl-3-isopropylidenyl-1,3-dihydro-2H-benzimidazol-2-one

60% Sodium hydride (0.758 g, 18.94 mmol, dispersion in oil) was suspended in DMF (60 ml) and isopropenyl-1,3-dihydro-2H-benzimidazol-2-one (J. Davoll, J. Chem. Soc., 1960, 308) (3.0 g, 17.22 mmol) was added portion-wise during 5 minutes. 4-Cyanobenzyl bromide (3.545 g, 18.08 mmol) was added in one go and the mixture left to stir at room temperature overnight. The mixture was concentrated in vacuo and ethyl acetate (200 ml) was added. The organic layer was washed with water (4×100 ml) separated and dried (MgSO$_4$). The organic layer was filtered and evaporated in vacuo to give a brown oil which solidified on standing. This solid was triturated with in ether (40 ml), filtered and dried to give a mustard coloured solid.

1-(4-Cyanophenyl)methyl-1,3-dihydro-2H-benzimidazol-2-one

Hydrochloric acid (d=1.84 g/ml, 10 ml) was added to a solution of 1-(4-cyanophenyl)methyl-3-isopropylidenyl-1,3-dihydro-2H-benzimidazol-2-one (6 g, 20.76 mmol) in ethanol (40 ml) and tetrahydrofuran (20 ml) and the mixture allowed to stand for 18 hours. The solvents were evaporated in vacuo to give a solid which was triturated with ethyl acetate to give a solid.

5-[4-(1,3-Dihydro-2H-benzimidazol-2-oxo-1-yl)methyl]phenyltetrazole

Sodium azide (3.36 g, 51.81 mmol) was added to a mixture of 1-(4-cyanophenyl)methyl-1,3-dihydro-2H-benzimidazol-2-one (2.15 g, 8.635 mmol) and triethylamine hydrochloride (7.12 g, 51.81 mmol) in dimethylformamide (20 ml) and heated at 125° C. for 3 hours, cooled the DMF removed in vacuo and the residue added to 2M hydrochloric acid (100 ml) and the resultant precipitate collected, washed with water (3×50 ml) and dried in vacuo at 80° C. to give a cream solid.

1-[4-(5-Methyl-1,3,4-oxadiazol-3-yl)phenyl]methyl-1,3-dihydro-2H-benzimidazol-2-one 5-[4-(1,3-Dihydro-2H-2-oxo-benzimidazol-1-yl)methyl]phenyltetrazole (2.42 g, 8.288 mmol) and acetic anhydride (100 ml) were heated under reflux under nitrogen for 2 hours, filtered hot, the solvent evaporated in vacuo and the residue dissolved in methanol (100 ml) and sodium methoxide (1 g, 18.5 mmol) added and the mixture stirred at room temperature for 16 hours. The solvent was then evaporated in vacuo and the residue suspended in 2M hydrochloric acid (100 ml) and stirred for 1 hour at room temperature. The resultant solid was isolated by filtration, washed with water (2×50 ml) and dried in vacuo at 80° C. to give a solid.

1-(2-Chloroethyl)-3-[4-(5-methyl-1,3,4-oxadiazol-3-yl phenyl]methyl-1,3-dihydro-2H-benzimidazol-2-one 1-[4-(5-Methyl-1,3,4-oxadiazol-3-yl)phenyl]methyl-1,3-dihydro-2H-benzimidazol-2-one (2.5 g, 8.17 mmol) was added to a suspension of 60% sodium hydride (0.36 g, 8.98 mmol, dispersion in oil) in N-methylpyrrolidinone (25 ml) and stirred for 0.75 hours. 1-Bromo-2-chloroethane (2.11 g, 14.7 mmol) was added and the mixture was allowed to stir at room temperature for 7 days, then water (300 ml) was added and the mixture stirred for 1 hour at room temperature. The resultant precipitate was isolated by filtration and dried in vacuo at 60° C. to give a solid.

1-[2-[4-(4-Fluorobenzoyl)-1-piperidinyl]-1-ethyl]-3-[4-(5-methyl-1,3,4-oxadiazol-3-yl)phenyl]methyl-1,3-dihydro-2H-benzimidazol-2-one hydrochloride 1-(2-Chloroethyl)-3-[4-(5-methyl-1,3,4-oxadiazol-3-yl) phenyl]methyl-1,3-dihydro-2H-benzimidazol-2-one (1 g, 2.714 mmol) 4-fluorobenzoylpiperidine p-toluenesulfonate (1.062 g, 2.8 mmol), potassium carbonate (1.16 g, 8.4 mmol) and N-methylpyrrolidinone (10 ml) were heated at 80° C. under nitrogen with magnetic stirring for 2 hours. Water (100 ml) was added to the mixture, which was then extracted with ethyl acetate (2×100 ml). The combined organic extracts were extracted with 2M hydrochloric acid (2×100 ml), the aqueous layer separated and basified with 12.5M sodium hydroxide and then extracted with ethyl acetate. The organic layer was washed with water, dried (MgSO$_4$).filtered and evaporated in vacuo to give a light brown oil, which was chromatographed on silica (EtOAc) to give a solid which was converted to a hydrochloride, m.p. 220–222° C.

EXAMPLE 4

1-(4-Aminophenyl)methyl-3-[2-[4-(4-fluorobenzoyl)-1-piperidinyl]-1-ethyl]-1,3-dihydro-2H-benzimidazol-2-one hydrochloride 1-[2-[4-(4-Fluorobenzoyl)-1-piperidinyl]-1-ethyl]-3-(4-nitrophenyl)methyl-1,3-dihydro-2H-benzimidazol-2-one (0.5 g, 0.996 mmol) in ethyl acetate (15 ml) and ethanol (15 ml) was hydrogenated at 60 psi over 10% palladium on charcoal (0.1 g) for 48 hours. The catalyst was removed by filtration and the solvent evaporated in vacuo to give an oily residue which was chromatographed over silica (EtOAc) to give a solid which was converted to a hydrochloride salt, m.p. 163–165° C.

EXAMPLE 5

4-Hydroxymethylbenzoic acid N,N-dimethylamide Isobutyl chloroformate (2.29 g, 16.7 mmol) was added to an ice cooled solution of 4-[(tetrahydropyran-2-yl)methyl]benzoic acid (Y. Kita, S. Akai, N. Ajimura, M. Yoshigi, T. Tsugoshi, H. Yasuda and Y. Tamura, J. Org. Chem., 1986, 22, 4150) and triethylamine (1.8 g, 17.5 mmol) in dry THF (40 ml) and stirred at 0° C. for 0.5 hours. 33% Dimethylamine in industrial methylated spirits (5 ml) was added and the mixture was allowed to warm to room temperature. The solvent was evaporated in vacuo, dissolved in ethyl acetate, washed with dilute aqueous citric acid solution then dilute aqueous sodium hydroxide solution, dried (MgSO$_4$), filtered and evaporated in vacuo to give a yellow oil which was dissolved in methanol (40 ml) and to this solution was added p-toluenesulfonic acid (0.1 equivalent) and stirred at room temerature for 1 hour. The solvent was then evaporated in vacuo and the residue dissolved in ethyl acetate, washed with dilute aqueous sodium hydroxide solution, dried (MgSO$_4$), filtered and evaporated in vacuo to give a pale yellow oil.

4-[[3-[2-[4-(4-Fluorobenzoyl)-1-piperidinyl]-1-ethyl]-1,3-dihydro-2H-2-oxo-benzimidazol-1-yl]methyl]benzoic acid N,N-dimethylamide monohydrochloride Methanesulfonyl chloride (1 g, 8.7 mmol) was added to a stirred solution of 4-hydroxymethylbenzoic acid N,N-dimethylamide (1.5 g, 8.4 mmol) and triethylamine (0.85 g, 8.4 mmol) in dichloromethane (35 ml) and stirred at room temperature for 0.75 hours, then the organic solution was washed with cold aqueous dilute hydrochloric acid, dried (MgSO$_4$), filtered and evaporated in vacuo to give an oil which was dissolved in dimethylformamide (5 ml) and added to a solution of 1-[2-[4-(4-fluorobenzoyl)-1-piperidinyl]-1-ethyl]-1,3-dihydro-2H-benzimidazol-2-one (1.5 g 4 mmol) and 60% sodium hydride (0.20 g, 4 mmol) in dimethylformamide (10 ml) and then stirred under nitrogen overnight. The dimethylformamide was evaporated in vacuo and the residue dissolved in ethyl acetate and then washed with aqueous lithium bromide solution, dried (MgSO$_4$), filtered and evaporated in vacuo to give an oil which was chromatographed on silica (EtOAc 95%, MeOH 5%) to give an oil which was dissolved in ethanol and treated with hydrochloric acid (d=1.84 g/ml, 2 ml), the ethanol evaporated in vacuo and the residue heated in ether and the undissolved solid isolated by filtration to give the hydrochloride, m.p. 214–216° C.

Similarly prepared were:

4-[[3-[2-[4-(4-Fluorobenzoyl)-1-piperidinyl]-1-ethyl]-1,3-dihydro-2H-2-oxo-benzimidazol-1-yl]methyl] benzoic acid N-methylamide hydrochloride, m.p. 146–148° C.

4-[[3-[2-[4-(4-Fluorobenzoyl)-1-piperidinyl]-1-ethyl]-1,3-dihydro-2H-2-oxo-benzimidazol-1-yl]methyl] benzoic acid amide hydrochloride, m.p. 166–168° C.

EXAMPLE 6

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 7

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

We claim:

1. A compound of the formula:

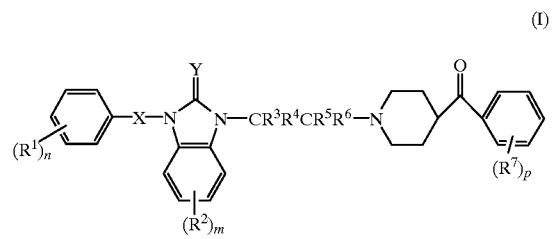

(I)

in which X is —CR'R"— or —C(O)— where R' and R" are each hydrogen, $C_{1-6}$ alkyl or optionally substituted phenyl, Y is oxygen or sulphur, $R^1$, $R^2$ and $R^7$ are each selected from halo, $C_{1-4}$ alkyl, $C_{1-4}$ alkoxy, trifluoromethyl, nitro, cyano, amino, phenyl, phenoxy, benzyl, benzyloxy, acylamino, $C_{1-4}$ alkylsulphonylamino, $C_{1-4}$ alkylthio, $C_{1-4}$ alkylsulphonyl, carboxamido, sulphonamido, hydroxy, methylenedioxy, carboxy, and heteroaryl, $R^3$, $R^4$, $R^5$ and $R^6$ are each hydrogen, $C_{1-6}$ alkyl or optionally substituted phenyl, n, m and p are each 0, 1, 2 or 3;

or a salt or ester thereof.

2. A compound according to claim 1 in which $R^1$, $R^2$ and $R^7$ are each selected from halo, $C_{1-4}$ alkyl, $C_{1-4}$ alkoxy, trifluoromethyl, nitro, cyano, amino, phenyl, phenoxy, benzyl, benzyloxy, acylamino, $C_{1-4}$ alkylsulphonylamino, $C_{1-4}$ alkylthio, $C_{1-4}$ alkylsulphonyl, carboxamido, hydroxy, methylenedioxy, carboxy, and heteroaryl.

3. A compound according to claim 2 in which $R^1$ is halo, heterocyclyl, $C_{1-4}$ alkyl or $C_{1-4}$ alkoxy, $R^2$ is halo, $C_{1-4}$ alkoxy or hydroxy, and $R^7$ is halo.

4. A compound according to claim 3 in which n and p are 1 and m is 0.

5. A compound according to claim 2 which is:

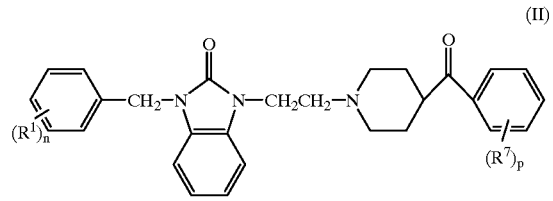

(II)

in which $R^1$ is halo, heterocyclyl, $C_{1-4}$ alkyl, $C_{1-4}$ alkoxy, cyano, nitro, carboxy, carboxamido or acetamido, $R^7$ is halo, and n and p are 1; and salts and esters thereof.

6. A pharmaceutical formulation comprising a therapeutically effective amount of a compound according to claim 1, or a pharmaceutically-acceptable salt or ester thereof, together with a pharmaceutically-acceptable diluent or carrier therefor.

* * * * *